United States Patent [19]

Joung

[11] 4,318,947
[45] Mar. 9, 1982

[54] POLYMER COATING AND CURING PROCESS FOR CATHETERS

[75] Inventor: Jong Joung, South Pasadena, Calif.

[73] Assignee: The Kendall Company, Boston, Mass.

[21] Appl. No.: 228,167

[22] Filed: Jan. 26, 1981

Related U.S. Application Data

[62] Division of Ser. No. 107,140, Dec. 26, 1979, Pat. No. 4,292,418.

[51] Int. Cl.$^3$ .................. A61M 25/00; B05D 3/02; B05D 1/18; B32B 27/00
[52] U.S. Cl. .................. 428/36; 128/349 R; 138/137; 138/145; 427/372.2; 427/430.1; 428/421; 428/492
[58] Field of Search .................. 138/145, 137; 128/349 R; 427/430.1, 372.2; 428/36, 421, 422, 492, 494

[56] References Cited

U.S. PATENT DOCUMENTS

| 3,434,869 | 3/1969 | Davidson | 128/349 R |
|---|---|---|---|
| 3,515,688 | 6/1970 | Rose | 528/399 |
| 3,856,561 | 12/1974 | Esemplare et al. | 427/430.1 |
| 3,922,378 | 11/1975 | Kline | 128/349 R |
| 4,119,094 | 10/1978 | Micklus et al. | 128/349 R |

OTHER PUBLICATIONS

"Poly(organophosphazenes)", Allcock, Chemtech, Sep. 1975, pp. 552-560.

*Primary Examiner*—William R. Dixon, Jr.

[57] ABSTRACT

The curing or cross-linking of fluorinated alkoxy phosphonitrile polymers with organic peroxides is accelerated by the use of a trialkyl aluminum or a dialkyl aluminum hydride. The coating with such polymers of biomedical articles such as embolectomy catheters or Foley retention catheters made of natural or synthetic rubber is facilitated by using for the coating a solution of such polymers in an organic solvent together with an organic peroxide and the new accelerating catalyst.

3 Claims, No Drawings

POLYMER COATING AND CURING PROCESS FOR CATHETERS

This is a division, of application Ser. No. 107,140 filed 12/26/79 now U.S. Pat. No. 4,292,418.

This invention relates to an improved method of cross-linking fluorinated alkoxy phosphonitrile polymers with organic peroxides and pertains more specifically to accelerating the cross-linking by using a trialkyl aluminum or a dialkyl aluminum hydride. Applicant believes that the alkyl aluminum compound functions as an accelerating catalyst. Solutions of such polymers in an organic solvent containing an organic peroxide and the alkyl aluminum compound can be used to coat catheters made of natural or synthetic rubber or elastomers.

Fluorinated alkoxy phosphonitrile polymers, also called fluorophosphazene polymers, are well known, being described inter alia in Rose U.S. Pat. No. 3,515,688 and in Allcock, Angewandte Chemie Int. Ed. Engl. 16, 147–156 (1977); Kyker Rubber, Chemistry and Technology, 47 32–46 (1974); Tate J. Polymer Sci. Symp. No. 48, 33–45 (1974); and Allcock, Chemtech 1975, pages 552–560. Such polymers, including copolymers in which not all of the fluoroalkoxy groups are identical to each other, possess a variety of desirable physical and chemical properties. They have been cross-linked or cured by heating with organic peroxides at elevated temperatures of the order of 250°–400° F. using magnesium oxide as an accelerator.

By the method of the present invention, curing or cross-linking of certain fluoroalkoxy phosphonitrile polymers with organic peroxides can be carried out at room temperature by using with them certain alkyl aluminum compounds. The polymers with which the present invention is useful are those containing randomly distributed repeating units having the structures:

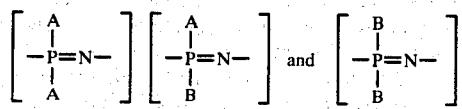

wherein A represents $X(CF_2)_m CH_2O-$ and B represents $Y(CF_2)_n CH_2O-$, X and Y each being selected from the group consisting of hydrogen and fluorine, and m and n each being an integer from 1 to 8 inclusive. The present invention is particularly advantageous in the case of elastomeric polymers having the foregoing composition, i.e., those in which the A and B are not identical to each other but differ in one or more respects within the limits of the definition given above.

The organic peroxides employed in the present invention can be any of those previously used in cross-linking or curing such polymers; among those suitable are benzoyl peroxide, acetyl peroxide, lauroyl peroxide, dicumyl peroxide, and $\alpha,\alpha'$-bis(t-butylperoxy)diisopropyl benzene, and mixtures of any two or more of the foregoing. Amounts of peroxide varying from 0.1 to 5% by weight of the polymer can be used.

The alkyl aluminum compounds which can be used in the present invention include those having the composition Al $R_1R_2R_3$ wherein $R_1$ is selected from the group consisting of hydrogen and alkyl having from 2 to 8 carbon atoms and $R_2$ and $R_3$ are alkyl having from 2 to 8 carbon atoms. Suitable alkyl aluminum compounds include diisobutyl aluminum hydride, triethyl aluminum, diisobutyl monoethyl aluminum, triisobutyl aluminum, and tri-n-octyl aluminum, as well as mixtures of any two or more of these. Amounts of alkyl aluminum compounds from 0.01 to 2% by weight of the polymer can be used. Applicant believes that there can also be employed alkyl aluminum compounds such as the foregoing which have been modified by reaction with transition metal halides such as titanium tetrachloride or titanium tetraiodide, known as Ziegler catalysts.

While the present invention can be practiced by incorporating the peroxide and the alkyl aluminum compound in the solid polymer, for example, by mixing the ingredients on a roll mill, it is generally preferred for maximum speed of cure to ensure thorough dispersion of both the peroxide and the alkyl aluminum compound throughout the polymer mass by dissolving the polymer in a suitable organic solvent such as a ketone, e.g., methyl isobutyl ketone, tetrahydrofuran, ethyl trifluoroacetate, dimethyl formamide, and liquid fluorocarbons. The peroxide can be dissolved in the same solvent as the polymer, but the alkyl aluminum compound used is most readily available in the form of a solution in a hydrocarbon such as hexane or octane; such solution can simply be mixed with the solution of polymer and peroxide.

Curing or cross-linking of the polymer in solution is particularly advantageous when the polymer is employed as a coating for a substrate, for example, as a coating for biomedical devices coming into contact with blood or other body fluids or tissue as in the case of a variety of implants and particularly the surfaces of catheters made of natural or synthetic elastomers or rubbers such as embolectomy catheters and urinary catheters, e.g., Foley retention catheters. When the polymer is in the form of a solution, its concentration can vary over any desired range depending upon the viscosity which is desired or convenient for the particular coating procedure used. Generally speaking, concentrations from 2 to 20% of polymer based on the weight of solvent are most useful.

The curing or cross-linking proceeds rapidly at room temperature when the polymer is in solution, being complete, as evidenced by loss of solubility and loss of thermoplastic properties as well as development of elastic properties, in a matter of an hour or two, as soon as the solvent has evaporated. When polymer in solid form is cured or cross-linked in accordance with the invention, greater time, up to 3 to 4 days is needed to complete the cure at room temperature. In each case, curing or cross-linking is further accelerated by heating to moderate temperatures of the order of 50° C. Higher temperatures can be employed but offer not great advantage. Curing or cross-linking of such polymers by means of the same organic peroxides either with or without magnesium oxide but without alkyl aluminum compound cannot successfully be carried out at room temperature even over very long periods of time.

The following specific examples serve to illustrate the nature of the invention without acting as a limitation upon its scope.

EXAMPLE 1

There was dissolved in 850 g of methyl isobutyl ketone 150 g of an elastomeric fluoroalkoxy phosphonitrile copolymer sold by Firestone Tire and Rubber Company under the trade name PNF 200 having the composition set forth in U.S. Pat. No. 3,515,688 and having randomly distributed repeating units having the structures defined above. With 100 g of the foregoing solution there was mixed 4 ml of a 5% by weight solution in methyl isobutyl ketone of α,α'-bis(t-butyl peroxy)diisopropyl benzene, after which there was mixed into the solution one ml of a 25% by weight solution in hexane of triisobutyl aluminum while avoiding contact of the mixture with moisture. The resulting mixed solution was poured into a Petri dish and allowed to stand at room temperature. The solution gradually gelled; after one-half hour it no longer flowed when the dish was tilted. Evaporation of the solvent was complete in 5 to 6 hours, at which time the polymer was a clear cross-linked elastomeric solid no longer soluble in methyl isobutyl ketone.

EXAMPLE 2

There was dissolved in 850 g of tetrahydrofuran 150 g of the same copolymer used in Example 1. With 100 g of the solution there was mixed 3 ml of the same peroxide solution as used in Example 1, after which there was mixed in one ml of a 20% by weight solution in hexane of triisobutyl aluminum while avoiding contact with moisture. The mixed solution was allowed to stand at room temperature and exhibited the same changes as did the solution of Example 1 to form a clear cross-linked elastomeric solid no longer soluble in tetrahydrofuran.

EXAMPLE 3

The copolymer solution of Example 1 was diluted with methyl isobutyl ketone to provide a solution containing 7% by weight of the copolymer. With one liter of this solution there were mixed, as described in Example 1, 10 ml of a 5% by weight solution of dicumyl peroxide in methyl ethyl ketone and 2 ml of a 25% by weight solution of triisobutyl aluminum in hexane. The mixed solution remained liquid for several hours at room temperature but after a Petri dish containing a layer of the solution had been allowed to stand for a day at room temperature, the solvents had evaporated and the product was in the form of a clear glossy solid which was partially cured or cross-linked as shown by the fact that it remained subject to some plastic deformation and also retained some solubility in methyl isobutyl ketone. Similar results were obtained by heating a layer of the mixed solution in a Petri dish for several hours at 50° C. Without the addition of the triisobutyl aluminum no cure at all occurred even after many days at 50° C.

EXAMPLE 4

A mass of the copolymer PNF 200 described in Example 1 was added to a roll mill. To the copolymer on the mill were added, for each 100 g of copolymer, 1 g of dicumyl peroxide, 2.5 ml of a 25% by weight solution of triisobutyl aluminum in hexane, and 10 ml of methyl isobutyl ketone; and the mixing was continued on the mill until puffy crumbs formed. The methyl isobutyl ketone served to promote dispersion of the peroxide and of the triisobutyl aluminum in the copolymer. The crumbs could be stored at room temperature for 24 hours, after which they could be molded to any desired shape by press molding at 10,000 psi. The molded articles could be cured or cross-linked by allowing to stand at room temperature for 3 to 4 days or by heating overnight at 50° C. to provide an elastomeric solid insoluble in methyl isobutyl ketone.

EXAMPLE 5

The copolymer solution of Example 1 was diluted with methyl isobutyl ketone to provide a solution containing 10% by weight of the copolymer. With one liter of this solution there were mixed as described in Example 1, sufficient 3% by weight solution in methyl isobutyl ketone of α,α'-bis(t-butyl peroxy) diisopropyl benzene to provide 2.4 parts by weight of peroxide per 100 parts of copolymer, after which there was mixed into the solution enough of a 20% by weight solution in hexane of diisobutyl aluminum hydride to provide 1 parts by weight of the aluminum compound per 100 parts of copolymer. When the mixed solution was allowed to stand at room temperature it exhibited the same changes as did the solution of Example 1 to provide an insoluble elastomeric cross-linked solid.

EXAMPLE 6

Three urinary catheters (14 Fr.) made of silicone rubber were cleaned with isopropyl alcohol and dried at 60° C. for one hour.

A 20 ml portion of a solution containing 12.5% by weight of the copolymer (PNF 200) described in Example 1 dissolved in methyl isobutyl ketone was diluted with 15 ml of methyl ethyl ketone and to the solution was added 1 ml of a 5% by weight solution of dicumyl peroxide in methyl isobutyl ketone, after which there was mixed in, while avoiding contact with moisture, 0.5 ml of a 25% by weight solution of triisobutyl aluminum in hexane.

The catheters were dipped in the mixed solution and dried at room temperature for three hours, after which the dipping and drying steps were repeated. The coatings were then cured by heating for two hours at 60° C. to produce a clear and uniform cured coating or film which was firmly attached to the catheter surface and which exhibited no peeling or separation from the catheter surface after the catheter was repeatedly stretched and allowed to retract. The coated catheters displayed anti-calculus, mucus-affinity and tissue-reaction properties very similar to those of the uncoated silicone catheters. Similar results can be obtained by coating catheters made of natural rubber such as latex rubber.

Because of the low temperature at which the cure or cross-linking of the copolymer coating is carried out, there is no appreciable change in the extent of cure of the previously cured silicone elastomer or natural rubber catheters. The coatings may vary in thickness over any desired range, being controlled by the concentration of the solution and the number of dips.

What is claimed is:

1. In a method of coating catheters made of natural or synthetic elastomers with a solution in an organic solvent of an organic peroxide cross-linking agent, and a linear polymer containing randomly distributed repeating units having the structures:

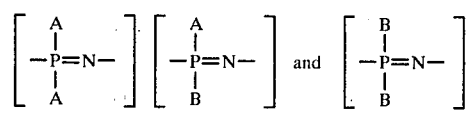

wherein A represents $X(CF_2)_mCH_2O-$ and B represents $Y(CF_2)_nCH_2O-$, X and Y each being selected from the group consisting of hydrogen and fluorine, and m and n each being an integer from 1 to 8 inclusive, and the improvement wherein there is included along with the organic peroxide an alkyl aluminum compound having the composition Al $R_1R_2R_3$ wherein $R_1$ is selected from the group consisting of hydrogen and alkyl having from 2 to 8 carbon atoms and $R_2$ and $R_3$ are alkyl having from 2 to 8 carbon atoms.

2. A method as claimed in claim 1 wherein said alkyl aluminum compound is trialkyl aluminum.

3. A method as claimed in claim 1 wherein said alkyl aluminum compound is triisobutyl aluminum.

* * * * *